United States Patent [19]
Feilden et al.

[11] Patent Number: 5,734,078
[45] Date of Patent: Mar. 31, 1998

[54] ALKYLATION PROCESS

[75] Inventors: Andrew D. Feilden, Selby; David J. Moreton, Hull; Charles B. Thomas, York, all of England

[73] Assignee: BP Chemicals (Additives) Limited, Hertfordshire, England

[21] Appl. No.: 740,675

[22] Filed: Oct. 31, 1996

[30] Foreign Application Priority Data

Nov. 1, 1995 [GB] United Kingdom ............... 9522359.0

[51] Int. Cl.$^6$ .................................................. C07C 65/10
[52] U.S. Cl. .................................... 562/477; 562/475
[58] Field of Search ......................... 562/477, 475

[56] References Cited

U.S. PATENT DOCUMENTS 5,415,792  5/1995  Campbell .
5,434,293  7/1995  Campbell et al. ................ 560/71

FOREIGN PATENT DOCUMENTS 2 542 732   9/1994  France .
269 619 A1  7/1989  Germany .
293 108 A5  8/1991  Germany .

*Primary Examiner*—Paul J. Killos
*Attorney, Agent, or Firm*—Nixon & Vanderhye

[57] ABSTRACT

A process for the production of an alkyl salicylic acid in which the alkyl substituent has at least 6 carbon atoms is disclosed, comprising reacting salicylic acid with an olefin having at least 6 carbon atoms at elevated temperature in the presence of sulphuric acid as a catalyst. Lubricating oil additives comprising a metal salt of such alkylated salicylic acids and a process for making them are also disclosed.

18 Claims, No Drawings

ALKYLATION PROCESS

The present invention relates in general to salicylic acid alkylation and in particular to the alkylation of salicylic acid by long-chain olefins. In an extension thereof the present invention relates also to the conversion of the alkylated salicylic acids by overbasing to lubricating oil additives.

Alkylated salicylic acids are conventionally prepared by alkylation of a phenol to form an alkylphenol followed by carboxylation of the alkylphenol by the Kolbe-Schmitt reaction to provide the alkylated salicyclic acid. In addition to the adverse economics attributable to the use of high temperatures and/or pressures, the Kolbe-Schmitt route to alkylated salicylic acids suffers from the problem that when substantially linear alkylation feeds are employed not all of the long-chain alkylphenol is readily carboxylated. This is because the long-chain orthoalkylphenol, which is generally formed along with the para-alkylphenol proportions typically ranging from 3:1 to 1:10, is less reactive in the Kolbe-Schmitt reaction: as a result conversion to alkylated salicyclic acid is considerably less than it might otherwise be.

Consequently other routes have been sought for the production of alkyl salicylic acids. Thus, for example, FR-A 2542732 discloses the monoalkylation of salicylic acid by reacting the acid in the presence of sulphuric acid as the catalyst with an ether of the general formula:-

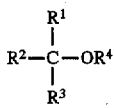
(I)

wherein $R^1$, $R^2$, $R^3$ and $R^4$, which may be the same or different, represent a saturated or unsaturated monovalent hydrocarbon radical containing from 1 to 4 carbon atoms. Whilst this route may be useful for the small-scale production of alkyl salicylic acids, the expense and scarcity of long carbon-chain ethers renders it economically unsuitable for the production of alkyl salicylic acids on an industrial scale.

DD-A-269619 and DD-A-293 108 both disclose the direct alkylation of salicylic acid with an olefin using an acidic ion exchange resin or polyphosphoric acid respectively as catalyst. Both documents explain that the use of sulphuric acid as a catalyst (in prior art processes not involving alkylation of the acid with an olefin) is undesirable because it has many disadvantages such as corrosion problems and side reactions.

U.S. Pat. No. 5,415,792 discloses alkylating an alkyl salicylate, for example methyl salicylate, and then subjecting the resulting alkylated alkyl salicylate to hydrolysis so as to provide an alkylated salicylic acid, it being perceived necessary for later formation of overbased products to start with the acid rather than the ester. Clearly hydrolysis of the alkylated alkyl salicylate prior to overbasing represents an economically undesirable extra step in the process for producing overbased products. However the invention of U.S. Pat. No. 5,415,792 is also directed in part to the discovery that alkylated alkyl salicylates can be overbased without hydrolysis of the ester functionality. The overbased alkylated alkyl salicylate composition is prepared by the process which comprises:

(a) combining into a diluent from about 15 to about 50 weight % of an alkylated alkyl salicylate based on the total weight of the alkylated alkyl salicylate/diluent composition wherein said alkylated alkyl salicylate is of the formula

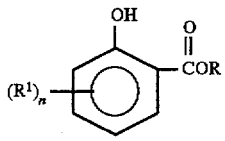

where R is alkyl of from 1 to about 6 carbon atoms; $R^1$ is an alkyl group of from about 15 to about 50 carbon atoms; and n is an integer from 1 to 2;

(b) combining a sufficient amount of an alkaline earth metal base into the composition produced in (a) above under conditions wherein the amount of alkaline earth metal is incorporated into the salicylate in excess of that necessary to neutralise the alkylated alkyl salicylate; and (c) optionally contacting from about 0.1 to about 1.5 molar equivalents of carbon dioxide based on each molar equivalent of alkylated alkyl salicylic acid under conditions wherein carbon dioxide is incorporated into the composition wherein the overbased composition has a TBN of from greater than 0 to about 300. The alkylated alkyl salicylate used in the aforesaid process may be prepared by alkylating an alkyl salicylate with an olefin of the appropriate chain length.

We have now found that alkyl salicylic acids, i.e. salicylic acid substituted in the aromatic nucleus by an alkyl group, can be prepared by alkylating salicylic acid, without conversion into its alkyl ester, with a long-chain olefin, using sulphuric acid as a catalyst. Contrary to what was reported in DD-A-269619 and 293108, we have found that sulphuric acid is a successful catalyst, and actually works better than acidic ion exchange resins for example.

Accordingly the present invention provides in one aspect a process for the production of an alkyl salicylic acid in which the alkyl substituent has at least 6 carbon atoms, comprising reacting salicylic acid with an olefin having at least 6 carbon atoms at elevated temperature in the presence of sulphuric acid as a catalyst.

Both straight-chain and branched-chain olefins, preferably 1-olefins, may be employed in the process of the invention. Preferred olefins are branched-chain olefins. Suitably the olefin has from 6 to 100, preferably from 6 to 50 and more preferably from 8 to 40 carbon atoms. Examples of higher olefins which may be used include polyisobutenes such as ULTRAVIS®, available from BP Chemicals Limited, or GLISSOPAL® available from BASF, which both have more than 70% of residual double bonds of the vinylidene type. Most preferred are olefins with from 10 to 25 carbon atoms. A suitable olefin is propylene tetramer, which comprises a mixture of $C_{12}$ olefins.

Commercial salicylic acid may be employed with or without further purification.

The conditions under which the reaction is carried out depend upon the nature of the olefin to be employed. The conditions to be described hereinafter are for 2-methyl-1-undecene, an example of a longer carbon chain branched 1-olefin. Using using other olefins different optimum reaction conditions may be desirable.

The sulphuric acid concentration may suitably be in the range from 60 to 95% (by volume), preferably from 70 to 85%, for example about 80%.

The elevated temperature at which the salicylic acid and the olefin are reacted is preferred to be 30° C. or more, and may suitably be in the range from 35° to 125° C. The optimum temperature within this range is dependent on the carbon chain length of the olefin. Typically, for a $C_{12}$ olefin the optimum temperature within the aforesaid range is from 50° to 70° C., for example about 60° C.

The duration of the reaction is usually not critical. A reaction time of about 2 to 4 hours, e.g. about 3 hours, is usually satisfactory.

The reaction may optionally be conducted in the presence of a solvent, but is generally in the absence of a solvent.

The alkyl salicylic acid may be recovered from the reaction mixture in known manner. For $C_{12}$ and higher salicylic acids, solvent extraction is generally desirable.

In another aspect the present invention provides a process for the production of a metal salt of a $C_6$ or greater alkyl salicylic acid suitable for use as a lubricating oil additive, which comprises the steps of:

(1) forming said $C_6$ or greater alkyl salicylic acid by a process as defined in any preceding claim, and (2) reacting said alkyl salicylic acid with a metal base in the presence of a solvent at elevated temperature.

A further aspect of the invention comprises the use of a metal salt of a $C_6$ or greater alkyl salicylic acid prepared by a process as defined above as a lubricating oil additive.

Step (2) of this process may be performed in the presence of carbon dioxide and optionally a carbonation catalyst. The metal base may suitably be either an alkali metal or an alkaline earth metal base, or a mixture of the two. Preferably the metal base is an alkaline earth metal base. Of the alkaline earth metals calcium, magnesium and barium are preferred and calcium is more preferred. The base may take the form of the oxide or the hydroxide. The calcium base may suitably be added as slaked lime, principally comprising calcium hydroxide.

The amount of base added may suitably be sufficient to provide either a normal salt or an overbased salt, a normal salt being one in which the ratio of the number of equivalents of the metal moiety to the number of equivalents of the alkyl salicylic acid moiety is about one and an overbased salt being one in which the ratio is usually greater than about 1.2 and as high as 4.5 or greater. It is preferred to produce the overbased salt.

The metal base may be added either in a single addition or in a plurality of additions at intermediate points during the reaction.

The solvent may be either (i) a polyhydric alcohol having 2 to 4 carbon atoms; (ii) a di-($C_2$ to $C_4$) glycol; (iii) a tri-($C_2$ to $C_4$) glycol; (iv) a mono- or polyalkylene glycol alkyl ether of the formula (I):

$$R^1(OR^2)_xOR^3 \tag{I}$$

wherein $R^1$ is a $C_1$ to $C_6$ alkyl group, $R^2$ is an alkylene group, $R^3$ is hydrogen or a $C_1$ to $C_6$ alkyl group and x is an integer from 1 to 6; (v) a monohydric alcohol having up to 20 carbon atoms; (vi) a ketone having up to 20 carbon atoms; (vii) a carboxylic acid ester having up to 10 carbon atoms; or (viii) an ether having up to 20 carbon atoms. Suitably the polyhydric alcohol (i) is a dihydric alcohol, for example ethylene glycol or propylene glycol, or a trihydric alcohol, for example glycerol. The di- or tri-($C_2$ to $C_4$) glycol may suitably be either diethylene glycol or triethylene glycol. The ether of the formula (I) may be the monomethyl or dimethyl ether of ethylene glycol, di-, tri- or tetraethylene glycol for example. Preferred solvents include ethylene glycol, 2-ethyl hexanol and a mixture of methanol and toluene.

In view of the intended use of the product of the process as a lubricating oil additive it is preferred to incorporate a lubricating oil as a supplemental diluent. The lubricating oil may suitably be an animal oil, a vegetable oil or a mineral oil. Suitably the lubricating oil is a petroleum-derived lubricating oil, such as a naphthenic base, a paraffin base or a mixed base oil. Solvent neutral (SN) oils are particularly suitable. Alternatively, the lubricating oil may be a synthetic oil, for example a synthetic ester or a polymeric hydrocarbon lubricating oil.

For the production of overbased metal salts it is preferred to react further with carbon dioxide, which may be added in the form of a gas or a solid, preferably in the form of a gas. When used in gaseous form, it may suitably be blown through the reaction mixture. Carbon dioxide addition is effected after the addition of metal base.

For the production of highly overbased metal salts the use of a carbonation catalyst is preferred. The catalyst may be either an inorganic compound or an organic compound, preferably an inorganic compound. Suitable inorganic compounds include hydrogen halides, metal halides, ammonium halides, metal alkanoates, ammonium alkanoates or mono-, di-, tri- or tetra-alkyl ammonium formates or alkanoates. Examples of suitable catalyst include calcium chloride, ammonium chloride, calcium acetate, ammonium acetate, zinc acetate and tetramethyl(ammonium acetate). Suitably the amount of catalyst employed may be up to 2.0% wt/wt.

For the production of highly overbased salts (salts having a Total Base Number (TBN) greater than 300) having an acceptable viscosity it is preferred to include also sufficient to provide from 2 to 40% by weight, based on the weight of the concentrate, of at least one compound which is either (i) a carboxylic acid or an acid anhydride, ester or salt thereof, the acid having the formula (II):

wherein $R^1$ is a $C_{10}$ to $C_{24}$ alkyl or alkenyl group and $R_2$ is either hydrogen, a $C_1$ to $C_4$ alkyl group or a —$CH_2COOH$ group, or (ii) a di- or polycarboxylic acid containing from 36 to 100 carbon atoms or an acid anhydride, ester or salt thereof. A preferred carboxylic acid of the formula (II) is stearic acid. The acid is preferably added in an amount in the range from greater than 10 to 35%, preferably from 12 to 25% by weight based on the weight of the concentrate.

For a fuller description of the production of highly overbased metal alkyl salicylates the reader is referred to EP-A-0351052, the contents of which are incorporated by reference herein.

Suitably the elevated temperature employed in the above reaction may be in the range from 50° to 200° C., preferably from 130° to 165° C.

The concentrate of the metal salt in the solvent may be recovered by conventional means, for example by distillative stripping. Finally, it is preferred to filter the concentrate so-obtained.

In another aspect the present invention provides a finished lubricating oil composition which composition comprises a major proportion of a lubricating oil and a minor proportion of an additive concentrate prepared by the process as hereinbefore described.

The amount of additive concentrate present in the finished lubricating oil will depend on the nature of the final use. Thus, for marine lubricating oils the amount of additive concentrate present may suitably be sufficient to provide a TBN of from 9 to 100 and for automobile engine lubricating oils the amount may suitably be sufficient to provide a TBN of from 4 to 20.

The finished lubricating oil may also contain effective amounts of one or more other types of conventional lubricating oil additives, for example viscosity index improver, anti-wear agent, antioxidant, dispersant, rust inhibitor, pour-point depressants and the like.

The invention will now be further illustrated by reference to the following Examples.

EXAMPLE 1

A 50 cm$^3$ one-necked round bottom flask, fitted with a condenser, was charged with 9 mmol (1.24 g) salicylic acid (obtained from Aldrich Chemical Co.) and 8 cm$^3$ 80% (by volume) sulphuric acid. Then 10 mmol (1.68 g; 1.1 equivalents) 2-methyl-1-undecene (obtained from Aldrich Chemical Co.) was added. The mixture was stirred, using a magnetic flea, at 40° C. for 3 hours. The mixture was thereafter allowed to cool and diluted with 40 cm$^3$ cold water. The product was extracted twice with 30 cm$^3$ diethyl ether. The organic layers were separated and the diethyl ether was removed on a rotary evaporator at a temperature of approximately 35° C. under vacuum (about 25 mm Hg vacuum). 2.5 g of product was recovered corresponding to an 87% yield based on the theoretical yield of the alkylsalicylic acid.

Mass spectrometric analysis of the methylated 5-(1,1-dimethyldecyl)-2-hydroxybenzoic acid (methylated using diazomethane) provided to following:

m/z320;(4); 194(16); 193(100); 161(60); 57(6); 41(10).

$^1$H N.M.R. (CDCl$_3$/TMS)δ[ppm]7.74(d 1H,J=2.5 Hz);7.44(d of d 1H,J=2.5, 8.7 Hz); 6.92(d, 1H,J=8.7 Hz); 1.4 (m 25H).

EXAMPLE 2

Example 1 was repeated except that the temperature was 50° C. instead of 40° C.

EXAMPLE 3

Example 1 was repeated except that the temperature was 60° C.

EXAMPLE 4

Example 1 was repeated except that the temperature was 65° C.

EXAMPLE 5

Example 1 was repeated except that the temperature was 75° C.

EXAMPLE 6

Example 1 was repeated except that the temperature was 90° C.

The results of Examples 1 to 6 are presented in the accompanying Table 1.

In Table 1 and subsequent Tables 2 to 4 there is a column headed 'Purity % alkylsalicylic acid'. The purity of the alkylsalicylic acid is calculated from the expression:

Purity=100×area of alkylsalicylic acid gas chromatographic peak/total area of all product gas chromatographic peaks.

Thus in the Tables below, the % yield of alkyl salicylic acid based on the theoretical yield is calculated as "Yield"× "Purity"/100.

It can be seen by reference to Table 1 that the optimum temperature for the reaction is from about 50 to about 70° C.

EXAMPLE 7

Example 3 was repeated except that instead of using 80% (by volume) sulphuric acid there was used 70% (by volume).

EXAMPLE 8

Example 3 was repeated except that instead of using 80% (by volume) sulphuric acid there was used 75% (by volume).

EXAMPLE 9

Example 3 was repeated except that instead of using 80% (by volume) sulphuric acid there was used 85% (by volume).

The results of Examples 7 to 9 are presented in Table 2 together with the result for Example 3. It can be seen by reference to the Table that the optimum sulphuric acid concentration is in the range from about 75% to 80% (by volume).

EXAMPLE 10

Example 3 was repeated except that instead of the reaction duration being 3 hours it was increased to 8 hours.

EXAMPLE 11

Example 3 was repeated except that instead of the reaction duration being 3 hours it was increased to 18 hours.

The remits of Examples 10 and 11 are presented in Table 3 together with the result for Example 3. It can be seen by reference to the Table that there is little to be gained in moving from 3 hours to much longer reaction times.

EXAMPLE 12

Example 3 was repeated except that instead of using 2-methyl-1-undecene, 1-hexene was used, and the reaction was room temperature instead of 60° C.

EXAMPLE 13

Example 12 was repeated except the reaction temperature was 30° C.

EXAMPLE 14

Example 12 was repeated except that the reaction temperature was 40° C.

EXAMPLE 15

Example 12 was repeated except that the reaction temperature was 55° C.

EXAMPLE 16

Example 3 was repeated except that 1-hexene was used instead of 2-methyl-1-undecene.

EXAMPLE 17

Example 12 was repeated except that the reaction duration was 1.5 hours instead of 3 hours.

EXAMPLE 18

Example 12 was repeated except that the reaction duration was 15 hours instead of 3 hours.

EXAMPLE 19

Example 12 was repeated except that 1-octene was used instead of 1-hexene.

EXAMPLE 20

Example 19 was repeated except that the reaction temperature was 65° C. instead of room temperature.

EXAMPLE 21

Example 12 was repeated except that 1-dodecene was used instead of 1-hexene.

EXAMPLE 22

Example 21 was repeated except that the reaction temperature was 55° C. instead of room temperature.

EXAMPLE 23

Example 22 was repeated except that the reaction temperature was 70° C. instead of 55° C.

EXAMPLE 24

Example 21 was repeated except that the reaction duration was 16 hours instead of 3 hours. Purity of the final product was not recorded; however it was noted that the product distribution was very different from that obtained with shorter reaction times.

EXAMPLE 25

Example 12 was repeated except that GLISSOPAL®, a polyisobutene having a molecular weight of 1000, was used instead of 1-hexene. Three sepcies were identified by 1H nmr: 5-polyisobutene salicylic acid, 5-sulfosalicylic acid and either 3-polyisobutene-5-sulfosalicylic acid or 3-sulfo-5-polyisobutene salicylic acid. Yield and purity values were not recorded.

The results of Examples 12 to 25 are presented in Table 4.

EXAMPLES 25–29

Sulphuric acid was compared with Amberlyst® 15 (a registered trade mark of Rohm and Haas Company), an acid ion exchange resin, as a catalyst in the alkylation of salicylic acid.

To a 50 cm³ round-bottomed flask fitted with a reflux condenser was added 0.01 moles of salicylic acid and the catalyst (8 cm³ of 80% sulphuric acid or 1 g Amberlyst® 15). To this mixture was added 0.01 moles of either 2-methyl-1-undecene or propylene tetramer. The reaction mixture was stirred using a magnetic flea at 60° C. for 3 hours. The work-ups on cooling involved: in the case of sulphuric acid, addition of about 40 cm³ water followed by extraction with diethyl ether, and in the case of Amberlyst® addition of diethyl ether followed by filtering off of the ion exchange resin. In both cases the diethyl ether was removed by rotary evaporator and the yield of all product calculated based on the theoretical yield of alkyl salicylate. GC analysis for performed after methylation by diazomethane, and the purity of the product calculated.

Results are given in Table 5 below. It can be seen that when Amberlyst® 15 is the catalyst, virtually no alkylsalicylic acid is formed.

In all the experiments below, 80% $H_2SO_4$ is used as the acid unless otherwise stated.

TABLE 1

| Example | Alkylating Agent | Temp °C. | Time h | Yield of total product (%) based on theoretical yield of alkylsalicylic acid only | Purity: % of total product that is alkylsalicylic acid |
|---|---|---|---|---|---|
| 1 | 2-methyl-1-undecene | 40 | 3 | 95% | 47% |
| 2 | 2-methyl-1-undecene | 50 | 3 | 98% | 53% |
| 3 | 2-methyl-1-undecene | 60 | 3 | 87% | 76% |
| 4 | 2-methyl-1-undecene | 65 | 3 | 89% | 60% |
| 5 | 2-methyl-1-undecene | 75 | 3 | 71% | 71% |
| 6 | 2-methyl-1-undecene | 90 | 3 | 68% | 75% |

TABLE 2

| Example | Alkylating Agent | Acid | Temp °C. | Time /h | Yield of total product (%) based on theoretical yield of alkylsalicylic acid only | Purity: % of total product that is alkylsalicylic acid |
|---|---|---|---|---|---|---|
| 3 | 2-methyl-1-undecene | $H_2SO_4$ 80% | 60 | 3 | 87% | 76% |
| 7 | 2-methyl-1-undecene | $H_2SO_4$ 70% | 60 | 3 | 95% | 27% |
| 8 | 2-methyl-1-undecene | $H_2SO_4$ 75% | 60 | 3 | 80% | 62% |
| 9 | 2-methyl-1-undecene | $H_2SO_4$ 85% | 60 | 3 | 66% | 32% |

TABLE 3

| Example | Alkylating Agent | Temp °C. | Time /h | Yield of total product (%) based on theoretical yield of alkylsalicylic acid only | Purity: % of total product that is alkylsalicylic acid |
|---|---|---|---|---|---|
| 3 | 2-methyl-1-undecene | 60 | 3 | 87% | 76% |
| 10 | 2-methyl-1-undecene | 60 | 8 | 73% | 60% |
| 11 | 2-methyl-1-undecene | 60 | 18 | 70% | 83% |

TABLE 4

| Example | Alkylating Agent | Temp °C. | Time /h | Yield of total product (%) based on theoretical yield of alkylsalicylic acid only | Purity: % of total product that is alkylsalicylic acid |
|---|---|---|---|---|---|
| 12 | 1-hexene | rt | 3 | 100% | 41% |
| 13 | 1-hexene | 30 | 3 | 96% | 61% |
| 14 | 1-hexene | 40 | 3 | 95% | 50% |
| 15 | 1-hexene | 55 | 3 | 79% | 57% |
| 16 | 1-hexene | 60 | 3 | 45% | 43% |

TABLE 4-continued

| Example | Alkylating Agent | Temp °C. | Time /h | Yield of total product (%) based on theoretical yield of alkylsalicylic acid only | Purity: % of total product that is alkylsalicylic acid |
|---|---|---|---|---|---|
| 17 | 1-hexene | rt | 1.5 | 90% | 38% |
| 18 | 1-hexene | rt | 15 | 96% | 53% |
| 19 | 1-octene | rt | 3 | 70% | 15% |
| 20 | 1-octene | 65 | 3 | 92% | 66% |
| 21 | 1-dodecene | rt | 3 | 91% | trace |
| 22 | 1-dodecene | 55 | 3 | 79% | trace |
| 23 | 1-dodecene | 70 | 3 | 70% | 8% |
| 24 | 1-dodecene | 60 | 16 | 80% | not recorded |
| 25 | Glissopal ® MW = 1000 | 60 | 3 | not recorded | not recorded | rt = room temperature

TABLE 5

| Example | Acid | Alkylating Agent | Temp °C. | Time h | Yield of total product (%) based on theoretical yield of alkylsalicylic acid only | Purity: % of total product that is alkylsalicylic acid |
|---|---|---|---|---|---|---|
| 26 | $H_2SO_4$ | 2-methyl-1-undecene | 60 | 3 | 89% | 60% |
| 27 | Amberlyst 15 | 2-methyl-1-undecene | 60 | 3 | 84% | 5% |
| 28 | $H_2SO_4$ | propylene tetramer | 60 | 3 | 80% | 80–85% |
| 29 | Amberlyst 15 | propylene tetramer | 60 | 3 | 82% | 0% |

We claim:

1. Process for the production of an alkyl salicylic acid in which the alkyl substituent has at least 6 carbon atoms, comprising reacting salicylic acid with an olefin having at least 6 carbon atoms at elevated temperature in the presence of sulphuric acid as a catalyst.

2. Process according to claim 1, wherein the olefin is a 1-olefin and/or a branched olefin.

3. Process according to claim 1 wherein the alkyl substituent of the salicylic acid/the olefin has from 6 to 100 carbon atoms.

4. Process according to claim 1 wherein the alkyl substituent of the salicylic acid/the olefin has from 6 to 50 carbon atoms.

5. Process according to claim 1 wherein the alkyl substituent of the salicylic acid/the olefin has from 8 to 40 carbon atoms.

6. Process according to claim 1 wherein the alkyl substituent of the salicylic acid/the olefin has from 10 to 25 carbon atoms.

7. Process according to claim 1, wherein the olefin is 2-methyl-1-undecene, 1-hexene, 1-dodecene or propylene tetramer.

8. Process according to claim 1, wherein the sulphuric acid concentration is 60–95% by volume.

9. Process according to claim 1, wherein the sulphuric acid concentration is 70–85% by volume.

10. Process according to claim 1, wherein the sulphuric acid concentration is about 80% by volume.

11. Process according to claim 1, wherein the elevated temperature is at least 30° C.

12. Process according to claim 1, wherein the elevated temperature is from 35° to 125° C.

13. Process according to claim 1, wherein the elevated temperature is from 50° to 70° C.

14. Process according to claim 1, wherein the reaction time is from 2 to 4 hours.

15. Process for the production of a metal salt of a $C_6$ or greater alkyl salicylic acid suitable for use as a lubricating oil additive, which comprises the steps of:

(1) forming said $C_6$ or greater alkyl salicylic acid by a process as defined in claim 1, and (2) reacting said alkyl salicylic acid with a metal base in the presence of a solvent at elevated temperature.

16. Process according to claim 15, wherein step (2) is performed in the presence of carbon dioxide.

17. Process according to claim 15, wherein the elevated temperature of step (2) is from 50° to 100° C.

18. A process according to claim 16, wherein step (2) is performed in othe presence of a carbonation catalyst.

* * * * *